(12) United States Patent
Arndt

(10) Patent No.: US 6,916,650 B2
(45) Date of Patent: Jul. 12, 2005

(54) TREATMENT OF SEED AND PLANTS WITH USEFUL BACTERIA

(75) Inventor: Wolfgang Arndt, Altenriet (DE)

(73) Assignee: Soùcon-Padena AG, Tubingen (DE)

( * ) Notice: Subject to any disclaimer, the term of this patent is extended or adjusted under 35 U.S.C. 154(b) by 259 days.

(21) Appl. No.: 10/156,243

(22) Filed: May 24, 2002

(65) Prior Publication Data
US 2003/0008776 A1 Jan. 9, 2003

Related U.S. Application Data

(63) Continuation of application No. PCT/EP00/10903, filed on Nov. 4, 2000.

(30) Foreign Application Priority Data

Nov. 29, 1999 (DE) .......................... 199 57 378

(51) Int. Cl.⁷ .......................... C12N 1/20; A01N 25/26; A01N 63/00
(52) U.S. Cl. ...................... 435/253.3; 504/100; 504/117
(58) Field of Search ........................ 435/253.3; 504/100, 504/117

(56) References Cited

U.S. PATENT DOCUMENTS 2,932,128 A   4/1960   Porter et al.

FOREIGN PATENT DOCUMENTS

DE   197 39 364 A1   9/1997

OTHER PUBLICATIONS

"Proradix–Seed Treatment for Potatoes," printed from Sourcon Padena AG (German) internet site, Sep. 2000.
W. Feet, et al., "Characterization of Exopolysaccharides Produced by Plant–Associated Fluorescent Pseudomonads," Applied and Environmental Microbiology, Mar. 1989, pp. 579–583.
M. Leeman, et al., "Induction of Systemic Resistance Against Fusarium Wilt of Radish by Lipopolysaccharides of Pseudomonas fluorescens," Phytopathology, vol. 85, No. 9, 1995, pp. 1–021–1027.
Copy of International Search Report from published WIPO application WO 01/40441 (PCT/EP00/10903, copy attached) Nov. 2000.

Primary Examiner—Herbert J. Lilling
(74) Attorney, Agent, or Firm—Knobbe, Martens, Olson & Bear, LLP

(57) ABSTRACT

An isolate of useful bacteria, preferably of the genus Pseudomonas, preferably of the species Proradix, is used for the treatment of plants and/or seed and incubated in a culture medium containing phosphorus compounds, nitrogen compounds and succinic acid. The solution can be used directly for spraying plants and/or seed, optionally followed by vacuum treatment. Furthermore, the solution can be vacuum-dried, the powder being dissolved in water prior to use.

13 Claims, No Drawings

TREATMENT OF SEED AND PLANTS WITH USEFUL BACTERIA

RELATED APPLICATION

This application is a continuation of International Patent Application PCT/EP00/10903, filed on Nov. 4, 2000 which designates the United States, published as WO 01/40441 in a language other than English.

BACKGROUND OF THE INVENTION

1. Field of the Invention

The present invention relates to the treatment of seed and plants with bacteria of the genus *Pseudomonas* and to a new species of the genus *Pseudomonas*, which is particularly suitable for this purpose.

2. Related Prior Art

A method of strengthening and protecting plants in which microorganisms of the genus *Pseudomonas* are employed is already disclosed in DE 197 39 364 A1.

In the known method, at least one resistance inductor together with a useful microorganism is introduced into the plants' nutrient medium or into the seed of the plant, resistance inductor and microorganism having a complementary positive effect on the plant.

An example of a useful microorganism which may be mentioned is the strain *Pseudomonas* sp. Psl of the genus *Pseudomonas fluorescens*, which is deposited at the DSMZ: (Deutsche Sammlung von Mikroorganismen und Zellkulturen [German Collection of Microorganisms and Cell Cultures]).

This publication furthermore describes a method of how to isolate such a useful microorganism from soil and roots. In this method, a dilution series from soil and roots is plated out, incubated and tested for fluorescent colonies which are then used in a screening against harmful fungi. Furthermore, a strain found by the known method is studied for its combination ability with resistance inductors. In this manner, the strain *Pseudomonas* sp. Psl has been found.

However, experiments carried out by the applicant of the present application have revealed that the treatment described in the publication stated at the outset is as yet unsatisfactory, which can be attributed, inter alia, to the fact that expensive resistance inductors must be employed together with the microorganism described, and it has furthermore been revealed that the protective action is frequently unsatisfactory.

U.S. Pat. No. 2,932,128 discloses a method for the treatment of seed in which the seed is moistened with a bacterial solution and then exposed to a vacuum in order to impregnate the seed.

SUMMARY OF THE INVENTION

In view of the above, it is an object of the present invention to provide novel solutions and methods and a novel microorganism for the treatment of seed and/or plants.

In accordance with one object, the invention relates to a *Pseudomonas* strain termed *Proradix*, which was deposited under the provisions of the Budapest Treaty on Mar. 11, 1999 at the DSMZ, 38124 Braunschweig under the deposit number *Pseudomonas* sp. *PRORADIX*-DSM 13134. The complete address of the Depository is:

DSMZ-Deutsche Sammlung von Mikroorganismen und Zellkulturen GmbH (DSMZ)
Mascheroder Weg 1 b
D38124 Braunschweig
Germany The *Pseudomonas* strain *Proradix*, which, according to studies by the DSMZ, probably constitutes another species within RNA group I of the Pseudomonadaceae, has been isolated by the inventor of the present application. A final attribution of *Proradix* was not possible, however, since only relatively little sequence similarity exists with validly described species of the genus *Pseudomonas*.

Field trials with the species *Proradix* have shown that it is a useful bacterium which is capable of colonizing the roots of useful plants, and there can exert its effect on the plant. It has been demonstrated in that connection that one application per vegetation period suffices and that additional resistance inductors can be dispensed with.

*Proradix* can be employed in a formulation as pickling liquor or as a powder and is suitable for the treatment of vegetable seed, in particular lamb's lettuce and carrots, of lawn seed and seed of woody species. Furthermore, it may be employed in green-manure seed for the biological soil conditioning and de-contamination, and for the seed treatment and immersion treatment of potatoes. In all these applications, *Proradix* has shown an improved quality compared to untreated control groups and in some cases also in comparison with chemical fungicides.

According to another object, the invention relates to a method for the preparation of a solution for the treatment of plants and/or seed, comprising the steps:

a) providing an isolate of useful bacteria, preferably of the genus *Pseudomonas*,
b) providing a culture medium containing phosphorus compounds, nitrogen compounds and succinic acid,
c) inoculating the culture medium with the isolate, and
d) incubating the culture medium at approximately 26–32° C. with gentle shaking for at least 50 hours.

The inventor has recognized that a solution thus prepared brings about a conditioning of the useful bacteria, which contributes to an improved protective action in the plants/seed treated with the bacteria. The inventor's current explanation of this conditioning effect is the induction of the formation of exopolysaccharides due to degradation products of the succinic acid. The exopolysaccharides are a protective substance forming a mucus which makes the bacteria particularly well storable on the seed/the plants.

In this context, the medium in which the bacteria are grown especially preferably contains $K_2HPO_4$, $KH_2PO_4$, $(NH_4)_2SO_4$, $MgSO_4$ and succinic acid, preferable contents being approximately 6.0 g of $K_2HPO_4$, approximately 3.0 g of $KH_2PO_4$, approximately 1.0 g of $(NH_4)_2SO_4$, approximately 0.2 g of $MgSO_4$ and approximately 4.0 g of succinic acid in approximately 1000 ml of deionized $H_2O$.

The inventor has found that exopolysaccharides are formed particularly rapidly in this medium, the cell density in a solution prepared by this method being less decisive for the seed treatment than the abovementioned conditioning.

On the other hand, the culture medium preferably contains glucose, preferred contents being approximately 6.0 g of $K_2HPO_4$, approximately 3.0 g of $KH_2PO_4$, approximately 1.5 g of $(NH_4)_2SO_4$, approximately 0.2 g of $MgSO_4$, approximately 2.0 g of glucose and approximately 4 g of succinic acid in approximately 1000 ml of deionized $H_2O$.

With this composition of the culture medium, a higher cell density can be achieved since the concentration of the carbon source present is higher. However, the inventor has recognized that exclusively glucose in the culture medium would rapidly lead to an acidic pH, which does not make possible further cultivation. This is why a mixture of glucose and succinic acid is chosen as carbon source so that the glucose is first metabolized, giving rise to a high cell density, but a low pH. After the glucose has been consumed, the succinic acid is metabolized, whereby the pH climbs, entailing survival, but slower growth, of the bacteria. This leads to the abovementioned formation of exopolysaccharides and the simultaneous improved action of microorganisms grown in such a solution.

Naturally, it is particularly preferred in this context to employ an isolate of the species Proradix.

According to a further object, the invention relates to a solution prepared by the method described so far.

On the other hand, it is also possible to dry the solution in vacuo, which is advantageous particularly when the culture medium contains glucose, so that the resultant powder contains bacteria in high concentrations. This powder can then be dissolved in water for use in the field, it being possible to employ the water treated thus for spraying seed, potatoes and the like.

According to yet another object, the present invention also relates to a powder prepared thus.

Furthermore, according to one object the invention relates to a method for the treatment of seeds in which seed moistened with the novel solution is temporarily exposed to sub-atmospheric pressure.

This is because the inventor of the present application has recognized that bacteria, in particular bacteria conditioned in accordance with the novel method, preferably the species Proradix, are suitable for the vacuum treatment of seed and lead to outstanding protective results.

On the other hand, the invention also relates to a method in which the seed/the plants is/are sprayed with a solution of the novel powder in water. This simple method, too, results in an effective protection of the treated plants.

Finally, according to another object the invention also relates to the use of the Pseudomonas strain Proradix for the treatment of plants, and to plants and seed treated by the novel method or in accordance with the novel use.

Further advantages will be seen from the following description of examples for growing and using the novel method and the species Proradix.

Of course, the features which have been mentioned hereinabove and are yet to be demonstrated hereinbelow can be used not only in the combinations stated specifically, but also in other combinations or alone, while still being within the scope of the present invention.

DESCRIPTION OF PREFERRED EMBODIMENTS

EXAMPLE 1

Isolation of the Species Proradix

Soil samples and roots were suspended and plated in dilution series in a selective medium so that individual colonies where obtained. Fluorescent colonies were employed for an in vitro screening, in which over 500 isolates were tested for inhibiting the growth of phytopathogenic fungi, in particular the soil-dwelling fungus Rhizoctonia. Candidates of interest were selected and tested on plants and subsequently in field trials.

In these tests, the inventor of the present application has isolated the species Proradix (DSM 13134) of the genus Pseudomonas which, according to identification by the DSMZ, is another species within the RNA group I of the Pseudomonadaceae. A summary of the strain characteristics as determined by the DSMZ is presented below in Table 1. A final attribution of Proradix was not possible, however, since only relatively little sequence similarity exists with validly described species of the genus Pseudomonas, but there is no doubt that the microorganism is a fluorescent representative of the Pseudomonas RNA group 1.

TABLE 1

Identification of the strain "Pseudomonas strain Proradix", (DSM ID 99-1)
Pseudomonas sp. (RNA group I)

| Properties of the strain | rods |
|---|---|
| cell shape | |
| width μm | 0.5–0.7 |
| length μm | 1.5–3.0 |
| mobility | + |
| flagellum | mono-polar, >1. |
| gram reaction | − |
| aminopeptidase (Cerny) | + |
| oxidase | + |
| catalase | + |
| urease(24 h) | − |
| pyocyanin | − |
| SUBSTRATE UTILIZATION | |
| citrate | + |
| malate | + |
| phenylacetate | + |
| d-glucose | + |
| maltose | − |
| mannit | + |
| arabinose | − |
| mannose | + |
| d-sorbitol | − |
| trehalose | + |
| m-inositol | + |
| citraconate | − |
| m-erythrite | − |
| 2-ketogluconate | + |
| raffinose | − |
| d-ribose | + |
| glycerol | + |
| growth at 41° C./45° C. | − |
| lysis by 3% KOH | + |
| nitrate reduction (to $NO_2$) | − |
| denitrification (to $N_2$) | − |
| levan from sucrose | − |
| lecithinase | + |
| fluorescence | + |
| ADH | + |
| hydrolysis of gelatine | + |
| Esculin | − |
| Tween 80 | + |

The profile of the cellular fatty acids was typical for the fluorescent representatives of the RNA group I of Pseudomonas. Partial sequencing of the 16SrDNA showed the highest similarity (97.1%) to Pseudomonas caricapapayae, P. ficusereccae, and P syringae. Physiological tests point to Pseudomonas fluorescens. These results are consistent with the designation of Proradix as a new species within RNA group I of Pseudomonadaceae.

EXAMPLE 2

Culturing the Isolate a) For the treatment of seeds, a Pseudomonas isolate, preferably the species Proradix, is inoculated into the following culture medium:

| | |
|---|---|
| K$_2$HPO$_4$ | 6.0 g |
| KH$_2$PO$_4$ | 3.0 g |
| (NH$_4$)$_2$SO$_4$ | 1.0 g |
| MgSO$_4$ | 0.2 g |
| succinic acid | 4.0 g | made up to 1000 ml with deionized H$_2$O.

The inoculated culture medium is incubated for 72 hours at 28° C./100 rpm; this gives a "liquid seed pickle".

b) To prepare a pulverulent formulation, a *Pseudomonas* isolate, preferably the species *Proradix*, is grown in the following culture medium:

| | |
|---|---|
| K$_2$HPO$_4$ | 6.0 g |
| KH$_2$PO$_4$ | 3.0 g |
| (NH$_4$)$_2$SO$_4$ | 1.5 g |
| MgSO$_4$ | 0.2 g |
| glucose | 2.0 g |
| succinic acid | 4.0 g | made up to 1000 ml with deionized H$_2$O.

Depending on the concentration of the inoculum, the culture medium inoculated thus is incubated for 65–70 hours at 28–30° C./100 rpm.

The solution is subsequently made into a powder in a vacuum drying oven. Formulation auxiliaries: dry skim milk and gum arabic.

c) Both culture media induce the formation of exopolysaccharides, while this formation takes place very rapidly in the case of the culture medium described under a), the cell concentration is of no importance, since seed treatment does not require large amounts of bacteria. However, a high cell concentration is indeed required in the case of the medium described under b), while the formation of exopolysaccharides is still desired. This is achieved by the mixture of glucose and succinic acid. First, the glucose is metabolized, which leads to a reduced pH, but to a high cell concentration. Once the glucose is consumed, the succinic acid is used as carbon source, and its degradation products lead to a rise in the pH and to the formation of exopolysaccharides.

EXAMPLE 3

Treatment of Seed with *Proradix*

One possible treatment consists in dissolving the powder prepared in Example 2b) in water and using it to spray the seed or the young plants before planting.

Furthermore, it is also possible to spray the solution prepared with the culture medium described in Example 2a) directly onto seed/plants before planting.

If the treated seed is still to be stored before planting, it is first moistened with the solution described in Example 2a), and then introduced into a sealable chamber in which a temporary vacuum is generated.

In this manner, the bacteria penetrate the seed and can still efficiently exert their protective action, even after prolonged storage.

EXAMPLE 4

Treatment of Young Lettuce Plants of Variety Garunda

Young plants of variety Garunda which are to be planted in one hectare of arable land are treated by pouring a solution of 50 ml *Proradix* ($10^7$ cfu/ml) per plant (Example 2b) over the young plants before they are planted up.

After harvesting, only 50% of the plants were not of marketable quality, while in the case of an untreated control 70% of the harvested plants were not of marketable quality.

In a comparative treatment with the chemical fungicides Switsch (NOVARTIS) (0.8 kg/ha) and Risolex (Spiess Urania) (3 l/ha), 58 and 48%, respectively, were not of marketable quality.

This result demonstrates that the lettuce is markedly less susceptible to black rot following treatment with *Proradix*, and the results are at least as good as in the case of treatment with chemical fungicides.

EXAMPLE 5

Treatment of Potatoes

*Proradix* is formulated as a powder as described in Example 2b), and the powder is dissolved in water as follows:

60 g of powder per 80 l of water for 1 ha with seed potatoes 60 g of powder ≙ $4 \times 10^{12}$ cfu The potato tubers are sprayed automatically with this solution and then planted directly. As an alternative, the potato tubers are dusted directly with the powder.

Comparative experiments between untreated potatoes (control), potatoes treated with *Proradix* and potatoes treated with FZB24 (Bayer Leverkusen, base: *Bacillus subtilis*) gave approximately identical yields of marketable produce per hectare. However, the quality showed that treatment with *Proradix* afforded reliable protection against black speck (Rhizoctonia attack), approximately 45% of the harvested potatoes showing no symptoms and a further approximately 45% showing minor symptoms. In the control group, the corresponding figures are 10% and 50%, and 25% and 50% in the case of FZB24.

Again, superiority of *Proradix* to the conventional crop protection products is demonstrated.

EXAMPLE 6

Treatment of Carrots Sold Clean

Carrot seed is moistened with *Proradix* seed treatment of Example 2a) as described in Example 3 and vacuum-treated (seed infiltration), stored and then sown.

The harvested carrots were stored for 4 months at 4° C., then—as is customary in sales—stored for two weeks at room temperature and finally assessed.

The quality showed 50% without blemish for the variety Nerac (untreated control: 18%) and 27% of useless carrots (control: 58%). The figures for the variety Mocum were 36% (control: 14%) and 46% (control: 54%), respectively.

Thus, the treatment of carrots sold clean with *Proradix* leads to a markedly increased product quality.

In conclusion, it can therefore be said that for the treatment of plants and/or seed an isolate of useful bacteria, preferably of the genus *Pseudomonas*, preferably the species *Proradix*, is provided and incubated in a culture medium containing phosphorus compounds, nitrogen compounds and succinic acid. The solution can be used directly for spraying plants and/or seed, optionally followed by vacuum treatment. Furthermore, the solution can be vacuum-dried, the powder being dissolved in water prior to use.

What is claimed is:

1. *Pseudomonas* isolated strain termed *Proradix*, which was deposited under the provisions of the Budapest Treaty on Mar. 11, 1999 at the DSMZ, 38124 Braunschweig, under the Accession number *PRORADIX*-DSM 13134.

2. A method for the preparation of a solution for the treatment of plants or seed, comprising the steps of:
   a) providing an isolate of the genus *Pseudomonas,*
   b) providing a culture medium containing phosphorus compounds, nitrogen compounds and succinic acid,
   c) inoculating the culture medium with the isolate, and
   d) incubating the culture medium at approximately 26–32° C. with gentle shaking for at least 50 hours,
wherein the bacterium is *Pseudomonas* strain *Proradix* (DSM 13134) of claim 1.

3. The method of claim 2, wherein, after incubation, the solution is vacuum-dried to prepare a powder.

4. A powder prepared by the method of claim 3.

5. A method for treating seed or plants, comprising the steps of:
   a) dissolving the powder of claim 4 in water, and
   b) spraying or immersion treatment of the seed or of seed potatoes with the solution of step a) or pouring the solution of step a) over young plants.

6. A method for treating plants or seed comprising the step of treating the plants or seed with the *Pseudomonas* strain *Proradix* of claim 1.

7. Seed or plants treated by the method of claim 5; whereby the seed or plants contains an effective amount of the *Pseudomonas* strain of claim 1 which contributes to an improved quality of the seed or plants.

8. Seed or plants treated by the method of claim 6; whereby the strain forms a protective storable mixture on the seed or plants.

9. The method of claim 2, wherein the culture medium contains $K_2HPO_4$, $KH_2PO_4$, $(NH_4)_2SO_4$, $MgSO_4$ and succinic acid.

10. The method of claim 9, wherein the culture medium contains glucose.

11. The method of claim 10, wherein the culture medium contains approximately 6.0 g of $K_2HPO_4$, approximately 3.0 g of $KH_2PO_4$, approximately 1.5 g of $(NH_4)_2SO_4$, approximately 0.2 g of $MgSO_4$, approximately 2.0 g of glucose and approximately 4.0 g of succinic acid in approximately 1000 ml of deionized $H_2O$.

12. A solution prepared by the method of claim 2.

13. A method of treating seed or plants, comprising the steps of:
   a) moistening the seed or plants with the solution of claim 12,
   b) applying a sub-atmospheric pressure to the seed or plants moistened above, and
   c) releasing the sub-atmospheric pressure.

* * * * *